United States Patent [19]

Weidman et al.

[11] Patent Number: 5,130,310

[45] Date of Patent: Jul. 14, 1992

[54] SUBSTITUTED BENZO[B]PYRANS, PROCESSES FOR THEIR PREPARATION, THEIR USE AND PHARMACEUTICAL PREPARATIONS BASED ON THESE COMPOUNDS

[75] Inventors: Klaus Weidman, Kronberg/Taunus; Heinrich C. Englert, Hofheim am Taunus; Bernward Schölkens, Kelkheim; Martin Bickel, Bad Homburg, all of Fed. Rep. of Germany

[73] Assignee: Hoechst Aktiengesellschaft, Frankfurt am Main, Fed. Rep. of Germany

[21] Appl. No.: 467,547

[22] Filed: Jan. 19, 1990

[30] Foreign Application Priority Data

Jan. 21, 1989 [DE] Fed. Rep. of Germany ....... 3901720

[51] Int. Cl.$^5$ ................. A61K 31/395; A61K 31/495; C07D 413/01
[52] U.S. Cl. ............... 514/233.5; 514/228.2; 514/255; 544/62; 544/151; 544/376
[58] Field of Search ................. 544/151; 514/233.5

[56] References Cited

U.S. PATENT DOCUMENTS

| | | | |
|---|---|---|---|
| 4,446,113 | 5/1984 | Evans et al. | 544/60 |
| 4,496,565 | 1/1985 | Evans et al. | 544/60 |
| 4,610,992 | 9/1986 | Evans et al. | 544/60 |

FOREIGN PATENT DOCUMENTS

| | | |
|---|---|---|
| 11227/88 | 9/1988 | Australia . |
| 0076075 | 4/1983 | European Pat. Off. . |
| 0107423 | 5/1984 | European Pat. Off. . |
| 0120427 | 10/1984 | European Pat. Off. . |
| 0120428 | 10/1984 | European Pat. Off. . |
| 0277611 | 8/1988 | European Pat. Off. . |
| 88/756 | 2/1988 | South Africa . |

OTHER PUBLICATIONS

Ashwood et al., J. Med. Chem., 29 (1986) pp. 2194-2201.

*Primary Examiner*—Johann Richter
*Attorney, Agent, or Firm*—Finnegan, Henderson, Farabow, Garrett and Dunner

[57] ABSTRACT

Benzo[b]pyran derivatives of the formula I

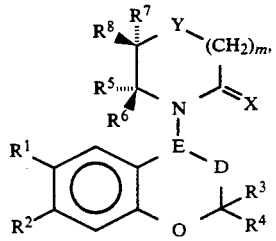

with
E—D equal to CH—CHOH or C=CH;
X equal to oxygen or sulfur;
Y equal to oxygen, sulfur, SO, $SO_2$ or $NR^9$;
$R^1$ equal to CN, $NO_2$, Hal, alkoxycarbonyl, $SO_{1-2}$-alkyl or $SO_{1-2}$-aryl;
$R^2$ equal to H, OH, alkoxy, alkyl, Hal, $NR^{10}R^{11}$;
$R^3/R^4$ equal to alkyl;
$R^5/R^6$ equal to alkyl, $(CH_2)_{1-6}$COO-alkyl, $(CH_2)_{1-6}$CONR$^{10}$R$^{11}$, $(CH_2)_{0-6}$COOH, $(CH_2)_{1-6}$CO-alkyl, $CO_2$-alkyl, alkylmercaptoalkyl, alkylsulfi(i)(o)nyl, hydroxyalkyl, mercaptoalkyl, aminoalkyl, N-(di)-alkylaminoalkyl or $(CH_2)_f$Ar with f equal to zero-3;
$R^7/R^8$ equal to hydrogen, alkyl or phenyl, and m equal to zero-2 are outstanding antihypertensives and spasmolytics. Preparation processes and use are described.

11 Claims, No Drawings

SUBSTITUTED BENZO[B]PYRANS, PROCESSES FOR THEIR PREPARATION, THEIR USE AND PHARMACEUTICAL PREPARATIONS BASED ON THESE COMPOUNDS

DESCRIPTION

The present invention relates to benzo[b]pyran derivatives of the formula I

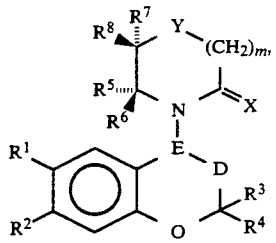

in which
E—D stands for
a) CH—CH(OH) or
b) C=CH,
X stands for O or S,
Y stands for O, S, SO, $SO_2$ and $NR^9$, where $R^9$ is hydrogen, $(C_1-C_6)$-alkyl, phenyl and benzyl, where the phenyl ring is unsubstituted or substituted by one or two identical or different radicals from the series comprising $(C_1-C_2)$-alkyl, $(C_1-C_2)$-alkoxy, F, Cl, Br, trifluoromethyl, CN, $NO_2$ or CO—$(C_1-C_2)$-alkyl,
$R^1$ stands for CN, $NO_2$, F, Cl, Br, $CF_3$, $(C_1-C_6)$-alkoxycarbonyl, $SO_n$—$(C_1-C_6)$-alkyl or $SO_n$—Ar; where n=1 or 2, Ar stands for an aromatic or heteroaromatic system which is unsubstituted or substituted by 1 to 3 identical or different radicals $(C_1-C_2)$-alkyl, $(C_1-C_2)$alkoxy, F, Cl, Br, trifluoromethyl, CN, $NO_2$, CO—$(C_1-C_2)$-alkyl or $SO_p$—$(C_1-C_2)$-alkyl, and p stands for 1 or 2,
$R^2$ stands for H, OH, $(C_1-C_2)$-alkoxy, $(C_1-C_2)$-alkyl, F, Cl, Br or $NR^{10}R^{11}$, where $R^{10}$ and $R^{11}$ are identical or different and stand for H, $(C_1-C_5)$-alkyl or $(C_1-C_5)$-alkylcarbonyl,
$R^3$ and $R^4$ are identical or different and stand for alkyl having 1–4 C atoms,
the abovementioned meanings of $R^1$ and $R^2$ may also be exchanged,
$R^5$ and $R^6$ are identical or different and stand for hydrogen, $(C_1-C_8)$-n-alkyl, $(C_1-C_{10})$-iso-alkyl, $(CH_2)_{1-6}CO_2(C_1-C_6)$-alkyl, —$(CH_2)_{1-6}CONR^{10}R^{11}$, where $R^{10}$ and $R^{11}$ have the above meanings, —$(CH_2)_{0-6}CO_2H$, —$(CH_2)_{1-6}$—CO—$(C_1-C_6)$-alkyl, —$CO_2$—$(C_1-C_6)$-alkyl, $(C_1-C_6)$-alkylmercapto-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_7)$-hydroxyalkyl, $(C_1-C_7)$-mercaptoalkyl, amino-$(C_1-C_7)$alkyl, N-$(C_1-C_4)$-alkylamino-$(C_1-C_7)$-alkyl, N,N-di$(C_1-C_4)$-alkylamino-$(C_1-C_7)$-alkyl or $(CH_2)_f$Ar, where Ar is an aromatic or heteroaromatic system which is unsubstituted or substituted by 1 to 3 identical or different radicals from the series comprising $(C_1-C_2)$-alkyl, hydroxyl, $(C_1-C_2)$-alkoxy, F, Cl, trifluoromethyl, CN, $NO_2$, CO—$(C_1-C_2)$-alkyl, $CO_2$—$(C_1-C_2)$-alkyl, $CO_2H$, $SO_p$—$(C_1-C_2)$-alkyl, p stands for 1 or 2, and f is zero, 1, 2 and 3, where, however, compounds are excluded in which $R^5$ and $R^6$ simultaneously are hydrogen,
$R^7$ and $R^8$ are identical or different and stand for hydrogen, $(C_1-C_3)$-alkyl or phenyl,
m is zero, 1 or 2; compounds being excluded, however, in which simultaneously
1. m=1
2. one of the two substituents $R^5$ or $R^6$ is equal to methyl and the other to hydrogen, $R^7$ and $R^8$ are hydrogen and
3. Y is oxygen, sulfur, NH or N—$(C_1-C_4)$-alkyl.

An aromatic system Ar is preferably understood to mean phenyl, naphthyl or biphenyl, a 5- or 6-membered heteroaromatic system Ar is preferably a radical of a 5- or 6-membered O-, N- and/or S-heterocyclic ring, in particular furyl, thienyl, isothiazolyl, oxazolyl, isoxazolyl, pyrazolyl, imidazolyl, indolyl, thiazolyl, pyridyl, pyrazinyl, pyrimidinyl, pyridazinyl or triazinyl.

Alkyl and radicals derived therefrom such as alkoxy, alkylmercapto, alkylsulfinyl or alkylsulfonyl may be straight-chain or branched.

Halogen is understood to mean F, Cl Br or I, preferably F and Cl.

In the compounds of the formula I, in which E—D stand for a) CH—CH(OH), the C atoms 3 and 4 of the 3,4-dihyrdo-2H-benzo[b]pyran system (also called "chroman system" in the following) are asymmetrically substituted. The invention relates only to those compounds which have opposite configurations on these centers. This means that the heterocyclic amide or thioamide ring as the substituent on carbon 4 and the OH group on carbon 3 are always orientated "trans" to one another. From the definitions for $R^5$ to $R^8$, it follows that the heterocyclic amide/thioamide moiety can carry two further centers of asymmetry in the α- and β-position to the nitrogen atom.

The invention thus relates to compounds having centers both with the R and also the S configuration. The same applies in the case in which $R^1$, $R^2$, $R^3$ or $R^4$ contain centers of asymmetry or, as substituents, themselves generate a center of asymmetry. The compounds may then be present as optical isomers, as diastereomers, as racemates or as a mixture thereof.

With the compounds of the formula I according to the invention, a class of substances having hypotensive properties has been found which above all differs from those known in that a heterocyclic amide or thioamide substituent carries additional substituents $R^5$ and $R^6$ and also $R^7$ and $R^8$ on carbon 4 of the chroman system in the abovementioned definition. This substitution leads to a considerable increase in the antihypertensive action with some compounds I in comparison to the already known compounds. Additionally, it has been observed that in some cases such an increase in action is accompanied by a reduction of the acute toxicity from which, collectively, an improvement in the therapeutic range can be derived. This is of outstanding importance especially in long-term therapy, such as the treatment of hypertonia, where it is in some cases necessary for a medicament to be taken for life. Animal experimental investigations show that the compounds of the formula I are suitable for the treatment of disturbances of the cardiovascular system, for example for the treatment of hypertonia, cardiac insufficiency or circulatory disturbances of the coronary system such as, for example, angina. Cerebral and peripheral circulatory disturbances are also favorably influenced. Moreover, other compounds I, which cause poorly pronounced circulatory effects, influence smooth muscular organs such as the uterus, bronchi, intestine and bile, the efferent urinary passages (ureter, bladder and urethra) in the sense of a spasmolysis. They are therefore suitable for the treatment of diseases which are associated with spasms of these organs, for example for the treatment of premature labor pain activity during pregnancy, colics of the ureter or the bile, obstructive airways disorders such as asthma, disturbances of the intestinal motility such as, for example, irritable colon or incontinence of the bladder.

Preferred compounds are those of the formula I, in which $R^1$, $R^2$, $R^3$ and $R^4$ have the abovementioned meanings, one of the two substituents $R^5$ and $R^6$ is hydrogen or methyl and the other has the above meaning and $R^7$, $R^8$, $R^9$, $R^{10}$, $R^{11}$, m, f, X and Y have the above meaning.

Particularly preferred compounds of the formula I are those in which $R^1$ stands for CN, $NO_2$, $SO_2$—$(C_1-C_4)$-alkyl, $(C_1-C_4)$-alkoxycarbonyl, fluorine, chlorine or $CF_3$, $R^2$ stands for H and $(C_1-C_2)$-alkoxy, $R^3$ and $R^4$ stand for methyl and ethyl, one of the two substituents $R^5$ and $R^6$ stands for hydrogen or methyl and the other stands for $(C_1-C_8)$-n-alkyl, $(C_1-C_{10})$-iso-alkyl, —$(CH_2)_{1-6}CO_2(C_1-C_6)$-alkyl or —$(CH_2)_{1-6}CONR^{10}R^{11}$, where $R^{10}$ and $R^{11}$ have the above meanings, —$(CH_2)_{1-6}$—$CO_2H$,—$(CH_2)_{1-6}$—CO—$(C_1-C_6)$-alkyl, —$CO_2H$ $(C_1-C_6)$- alkylmercapto-$(C_1-C_6)$-alkyl,$(C_1-C_6)$-alkylsulfinyl-$(C_1-C_6)$-alkyl, $(C_1-C_6)$-alkylsulfonyl-$(C_1-C_6)$-alkyl, $(C_1-C_7)$-hydroxyalkyl, $(C_1-C_7)$-mercaptoalkyl, amino-$(C_1-C_7)$-alkyl, N-$(C_1-C_4)$-alkylamino-$(C_1-C_7)$-alkyl, N,N-di$(C_1-C_4)$-alkylamino-$(C_1-C_7)$-alkyl or $(CH_2)_f$Ar, where Ar is an aromatic or heteroaromatic system which is unsubstituted or substituted by 1 to 3 identical or different radicals from the series comprising $(C_1-C_2)$-alkyl, hydroxyl, $(C_1-C_2)$-alkoxy, F, Cl, trifluoromethyl, CN, $NO_2$, CO—$(C_1-C_2)$-alkyl, $CO_2$—$(C_1-C_2)$-alkyl, $CO_2H$ or $SO_p$—$(C_1-C_2)$-alkyl, p stands for 1 or 2, and f is zero, 1, 2 and 3, $R^7$ and $R^8$ are identical or different and stand for hydrogen, $(C_1-C_3)$-alkyl and phenyl, $R^9$ stands for H, $(C_1-C_4)$-alkyl, phenyl and benzyl, where the phenyl ring is unsubstituted or substituted by one or two identical or different radicals from the series $(C_1-C_2)$-alkyl, $(C_1-C_2)$-alkoxy, F, Cl, trifluoromethyl, CN, $NO_2$ or CO—$(C_1-C_2)$-alkyl, m is zero or 1, X stands for O or S and Y stands for O, SO, $SO_2$ or $NR^9$, in which $R^9$ is as defined above.

Particularly preferred compounds of the formula I are likewise those in which $R^1$ stands for $SO_2$ phenyl, where phenyl is unsubstituted or substituted by 1 to 3 substituents from the series comprising $(C_1-C_2)$-alkyl, $(C_1-C_2)$-alkoxy, F, Cl, Br, trifluoromethyl, CN, $NO_2$, CO—$(C_1-C_2)$-alkyl or $SO_p$—$(C_1-C_2)$-alkyl, and p stands for 1 or 2, $R^2$ stands for H and $(C_1-C_2)$-alkoxy, $R^3$ and $R^4$ stand for methyl and ethyl, one of the two substituents $R^5$ and $R^6$ stands for hydrogen or methyl and the other stands for $(C_1-C_8)$-n-alkyl, $(C_1-C_{10})$-iso-alkyl, —$(CH_2)_{1-6}CO_2(C_1-C_6)$-alkyl or —$(CH_2)_{1-6}CONR^{10}R^{11}$, where $R^{10}$ and $R^{11}$ have the above meanings, —$(CH_2)_{1-6}$—$CO_2H$, —$(CH_2)_{1-6}$—CO—$(C_1-C_6)$-alkyl, —$CO_2H$, $(C_1-C_6)$-alkylmercapto-$(C_1-C_6)$-alkyl, $(C_1-C_6)$-alkylsulfinyl-$(C_1-C_6)$-alkyl, $(C_1-C_6)$-alkylsulfonyl-$(C_1-C_6)$-alkyl, $(C_1-C_7)$-hydroxyalkyl, $(C_1-C_7)$-mercaptoalkyl, amino-$(C_1-C_7)$-alkyl, N-$(C_1-C_4)$-alkylamino-$(C_1-C_7)$-alkyl, N,N-di$(C_1-C_4)$-alkylamino-$(C_1-C_7)$-alkyl or $(CH_2)_f$Ar, where Ar is an aromatic or heteroaromatic system which is unsubstituted or substituted by 1 to 3 identical or different radicals from the series comprising $(C_1-C_2)$-alkyl, hydroxyl, $(C_1-C_2)$-alkoxy, F, Cl, trifluoromethyl, CN, $NO_2$, CO—$(C_1-C_2)$-alkyl, $CO_2$—$(C_1-C_2)$-alkyl, $CO_2H$ or $SO_p$—$(C_1-C_2)$-alkyl, p stands for 1 or 2, and f is zero, 1, 2 and 3, $R^7$ and $R^8$ are identical or different and stand for hydrogen, $(C_1-C_3)$-alkyl and phenyl, $R^9$ stands for H, $(C_1-C_4)$-alkyl, phenyl and benzyl, where the phenyl ring is unsubstituted or substituted by one or two identical or different radicals from the series $(C_1-C_2)$-alkyl, $(C_1-C_2)$-alkoxy, F, Cl, trifluoromethyl, CN, $NO_2$ or CO—$(C_1-C_2)$-alkyl, m is zero or 1, X stands for O or S and Y stands for O, SO, $SO_2$ or $NR^9$, in which $R^9$ has the above meaning.

Very particularly preferred compounds of the formula I are those in which E—D is defined as above under a) and $R^1$ stands for CN or $SO_2CH_3$, $R_2$ stands for H, $R^3$ and $R^4$ stand for methyl, one of the substituents $R^5$ and $R^6$ is hydrogen and the other stands for $(C_1-C_6)$-n-alkyl, $(C_1-C_8)$-iso-alkyl, phenyl, benzyl or pyridyl, where the aromatic or heteroaromatic systems are unsubstituted or substituted by a radical from the series comprising $(C_1-C_2)$-alkyl, $(C_1-C_2)$-alkoxy, chlorine, fluorine, $CF_3$ and CN, $R^7$ and $R^8$ stand for hydrogen, m is zero, X stands for O and Y stands for O or $NR^9$, in which $R^9$ is $(C_1-C_4)$-alkyl and benzyl.

Very particularly preferred compounds of the formula I are likewise those in which E—D is defined as above under a) and $R^1$ stands for $SO_2$-phenyl, $R^2$ stands for hydrogen, $R^3$ and $R^4$ stand for methyl, one of the substituents $R^5$ and $R^6$ is hydrogen and the other stands for $(C_1-C_6)$-n-alkyl, $(C_1-C_8)$-iso-alkyl, phenyl, benzyl or pyridyl, where the aromatic or heteroaromatic systems are unsubstituted or substituted by a radical from the series comprising $(C_1-C_2)$-alkyl, $(C_1-C_2)$-alkoxy, chlorine, fluorine, $CF_3$ and CN, $R^7$ and $R^8$ stand for hydrogen, m is zero, X stands for O and Y stands for O or $N^9$, in which $R^9$ is $(C_1-C_4)$-alkyl and benzyl.

The invention furthermore relates to a process for the preparation of the compounds I, in which E—D is defined as under a), which comprises a) reacting a compound of the formula II

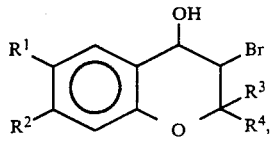

in which $R^1$, $R^2$, $R^3$ and $R^4$ have the abovementioned meanings, with a lactam or thiolactam of the formula III

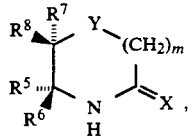

in which $R^5$, $R^6$, $R^7$, $R^8$, X, Y and m have the above-mentioned meanings, or by b) reacting a compound of the formula IV

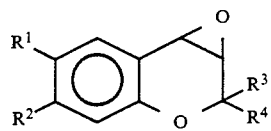

in which $R^1$, $R^2$, $R^3$ and $R^4$ have the abovementioned meanings, with a heterocyclic amide or thioamide of the formula III

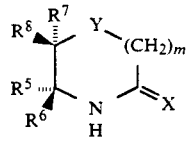

or by c) reacting a compound of the formula II

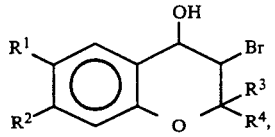

in which $R^1$, $R_2$, $R^3$ and $R^4$ have the abovementioned meanings, with a compound of the formula V

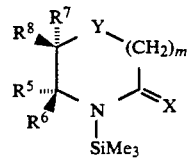

in which $R^5$, $R^6$, $R^7$, $R^8$, X, Y and m have the above-mentioned meanings, or d) bringing to reaction a compound of the formula IV

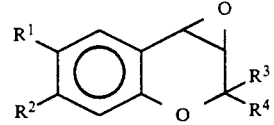

in which $R^1$, $R^2$, $R^3$ and $R^4$ have the above meanings, with a compound of the formula V

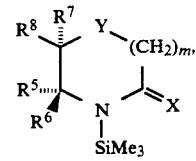

in which $R^5$, $R^6$, $R^7$, $R^8$, X, Y and m have the above-mentioned meanings, or e) acylating a compound of the formula VI

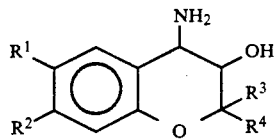

in which $R^1$, $R^2$, $R^3$, and $R^4$ have the above-mentioned meanings, to the compound of the formula VII

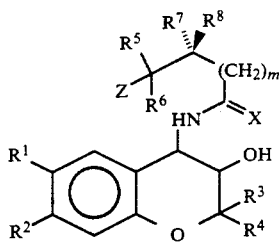

in which $R^1$, $R^2$, $R^3$, $R^4$, $R^5$, $R^6$, $R^7$, $R^8$, X and m are as defined above and Z has the meaning of a leaving group such as chlorine or bromine, and cyclizing this to give a compound of the formula I.

The processes indicated under a)–d) are equally suitable for the preparation of compounds of the formula I, in which E—D is defined as under b).

If the compounds I are prepared according to the methods a) and b), this is done by reacting the compounds II and IV with the compounds III in a suitable solvent such as, for example, dimethyl sulfoxide, dimethylformamide, tetrahydrofuran or N-alkylated ureas, for example 1,3-dimethyltetrahydro-2(1H)-pyrimidinone (DMPU), preferably under the influence of strong bases such as, for example, sodium hydride, potassium hydride, lithium diisopropylamide, lithium bis(trimethylsilyl)amide, potassium bis(dimethylsilyl)amide, or similar bases which are known to be suitable for lactam-N-alkylations. The reaction temperature in this case can be varied within a wide range, and the reaction is preferably carried out at temperatures between 0° C. and room temperature or at temperatures which may be slightly above room temperature.

Compounds which can only be prepared with difficulty by methods a) or b) can be made accessible by processes c) or d). In this case, the compounds II or IV are stirred together with the compounds V in the presence of a desilylating agent such as potassium tert.-butylate or tetrabutylammonium fluoride trihydrate in a dipolar aprotic solvent such as THF and the like. It is also possible to carry out the reaction without additions of solvents in the presence of an excess of the partly liquid compounds V. The temperature in this case can vary within wide limits.

Thus, in many cases the compounds I according to the invention are obtained even at room temperature, in other cases only after heating to 60°-80° C. In some cases, even still higher temperatures are necessary.

Compounds of the formula III are commercially available in many cases or can be synthesized simply by methods known from the literature.

The silyl compounds of the formula V can be prepared from compounds of the formula III in a manner known per se, for example by heating with 1,1,1,3,3,3-hexamethyldisilazane and subsequent distillation.

When using racemic or also optically uniform heterocyclic amides or thioamides of the formula III or their silyl derivatives of the formula V, at least two novel products of the formula I are obtained. These products can be separated by the customary methods, such as crystallization or chromatography, and in many cases a combination of the two methods has also proved favorable. The products can then be allocated the respective total configuration by means of customary physical investigations, such as, for example, x-ray structural analysis or NMR spectroscopy. Optically uniform, i.e. enantiomerically pure compounds I can be obtained by subsequent racemate cleavage. However, if already enantiomerically pure heterocyclic amides or thioamides III or the silyl derivatives V are used, the diasteromeric compounds I are likewise obtained in enantiomerically pure form and a racemate cleavage is superfluous.

The bromohydrins II or the epoxides IV are known in many cases (cf. here the Patent Specifications cited below or J. Med. Chem. 1986, 29, 2194–2201) or can be prepared analogously by methods described there. The heterocyclic amides or thioamides of the formula III are known in many cases or can be prepared easily by methods known from the literature. For example, compounds of the formula III, in which Y=0, X=0 and m=zero, can be obtained by bringing to reaction the 2-amino-1-alkanols of the formula VIII with phosgene equivalents, such as diphenyl carbonate, diethyl carbonate, N,N-carbonyldiimidazole or trichloromethyl chloroformate in a suitable solvent (cf., for example, J.Org. Chem. 1985, 50, 1830–1835).

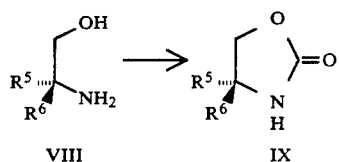

Analogous compounds, in which X is S, are obtained correspondingly using thiophosgene equivalents.

Compounds of the formula III, in which Y is NR$^9$, X is O or S and m is zero, can be prepared, for example, by the following equation.

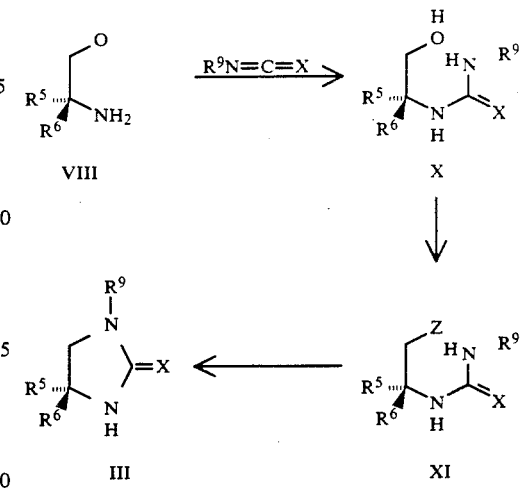

Substituted 2-amino-1-alkanols of the formula VIII are converted using isocyanates or isothiocyanates into theureas or thioureas of the formula X, from which the compounds XI are obtained using halogenating reagents such as thionyl chloride. The substituted imidazolidin2-ones of the formula III are accessible by subsequent ring closure reaction.

In J. Med. Chem. 1986, 29, 2194–2201, compounds are described which are close to the compounds according to the invention. They are summarized there under the following general formulae:

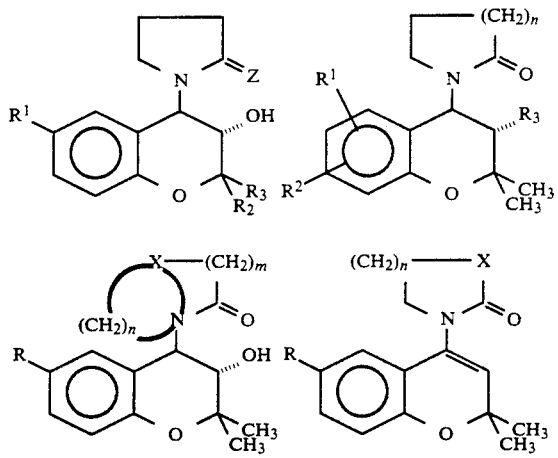

with R$^1$, R$^2$, R$^3$, X, Z, n, m and R having the meanings shown there. A large part of these compounds is also described in various patent applications, and those to be mentioned in this connection are: EP 107,423, EP 120,427, EP 76,075, EP 120,428 and EP 277,611.

In EP 107,423 and EP 277,611, compounds are described which are very close to the compounds according to the invention.

It is known of these compounds that they are able to lower a pathologically increased blood pressure by relaxing the smooth vascular musculature or protecting it against or rendering it insensitive to pressor stimuli.

In EP 0,107,423, chroman derivatives of the formula A

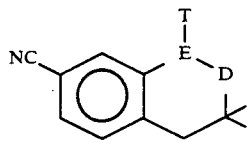

are described, where

T may be 3-oxazolidinyl-2-one, 3-thiazolidinyl-2-one, 1-morpholinyl-2-one, 1-thiomorpholinyl-2-one and N-substituted 1-piperazinyl-2-one and E—D may be CH—CH(OH) or CH=CH.

However, these compounds do not carry any substituents in the heterocyclic amide or thioamide ring.

In EP 277,611 compounds of the formula B

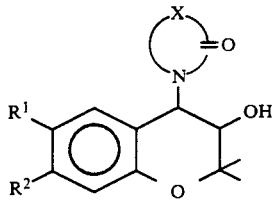

are described, in which X stands for a chain $(CH_2)_m$ which is substituted by a $(C_1-C_2)$-alkyl group and which may be interrupted by a heteroatom Y which stands for O, S or NR, and where m stands for 2, 3 or 4. According to the definition, thus only compounds are described in which a heteroatom Y is a middle member in a $(CH_2)_m$ chain, but is not at the end, as the present invention exclusively aims for the case in which m is zero.

The heterocyclic amides and thioamides described here offer the advantage that, for their synthesis, inter alia, substituted optically active 2-amino-1-alkanols are inexpensively available from natural and synthetic α-amino acids and their derivatives according to reduction methods known from the literature.

The advantage of the use of heterocyclic amide building blocks prepared from chiral 2-amino-1-alkanols, such as substituted imidazolidin-2-ones and 4-substituted oxazolidin-2-ones consists in that the diastereomeric compounds of the formula I are also obtained in enantiomerically pure form and a racemate cleavage is superfluous.

The use of the derivatives of the enantiomerically pure α-amino acids makes possible not only the specific prestatement of the configuration in the α-position to the amide N atom, but ensures in particular the introduction of a large number of substituents $R^5$ and $R^6$, where in these cases one of the substituents is hydrogen.

One of the substituents $R^5$ and $R^6$ can thus be traced back to the variable radicals of the α-amino acids in a number of cases, for example, a substituents pattern

| | |
|---|---|
| $R^5$ = methyl<br>$R^6$ = H | can be traced back to D-alanine, |
| $R^5$ = H<br>$R^6$ = methyl | can be traced back to L-alanine, |
| $R^5$ = isopropyl<br>$R^6$ = H | can be traced back to D-valine | and so on.

The compounds of the formula I according to the invention are, as already mentioned, antihypertensives and spasmolytics which can be employed as pharmaceuticals in human and veterinary medicine. They are administered enterally, for example orally or parenterally (such as, for example, by injection into the vascular system, for example intravenously) in dosages of at least 0.001 mg/kg/day, preferably 0.005 mg and in particular 0.5 mg/kg/day up to a maximum of 10 mg/kg/day, preferably 5 mg/kg/day and in particular 2 mg/kg/day in capsules, coated tablets, tablets, powders, suppositories or solutions with additions or without additions of galenical auxiliaries, in each case relative to a weight of about 75 kg. They are suitable for the treatment of hypertonia, alone or in combination with other antihypertensive pharmaceuticals, such as, for example, diuretics, Ca antagonists, ACE inhibitors or β-blockers. These data relate to a human of weight 75 kg.

EXAMPLE 1 a) N-Trimethylsilyl-4S-benzyl -oxazolidin-2-one

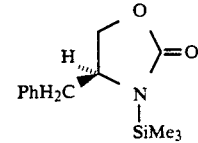

9.9 g (55 mmol) of 4S-benzyloxazolidin-2-one are suspended in 50 ml of hexamethyldisilazane under argon and the mixture is slowly heated to 125° C., the initially 2-phase system changing to a clear solution after about 2.5 h. After a further 7.5 h at 125° C., the solution is freed from excess hexamethyldisilazane in vacuo and the residue is distilled with the oil pump.

B.p. $_{0.1}$=151° C.,

Colorless crystals, m.p. 52°-54° C.

b) 2,2-dimethyl-3,4-dihydro-6-phenylsulfonyl-trans[3-hydroxy-4-(4'S-benzyl-3-oxazolidin-yl-2-one)]-2H-benzo[b]pyran, isomer A and B

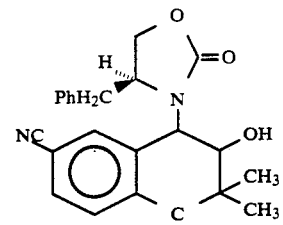

31.5 g (20 mmol) of tetra-n-butylammonium fluoride trihydrate are added in portions with stirring at room temperature to a solution of 4.0 g (20 mmol) of 2,2-dimethyl-3,4-dihydro-3,4-epoxy-6-cyano-2Hbenzo[b]-pyran and 5.5 g (22 mmol) of N-trimethylsilyl-4S-benzyloxazolidin-2-one in 100 ml of N,N-dimethylacetamide. The mixture is then warmed at 70° C. for 2 hours, and discharged into 200 ml of aqueous NH$_4$Cl solution at room temperature. After extracting with ethyl acetate, drying and concentrating in vacuo, the residue is chromatographed on silica gel using cyclohexane and ethyl acetate (1:1). Appropriate fractions are concentrated and the product mixture of the two isomers is made to crystallize using ethyl acetate. According to ¹H-NMR (270 MHz) a nearly 50:50 mixture of isomer A and B is present. M.p. 188°–190° C.

EXAMPLE 2 a) 4R-Ethyl-oxazolidin-2-one

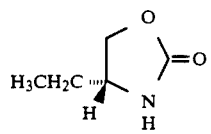

24.3 g (0.15 mol) of N,N-carbonyldiimidazole are added in portions with stirring at room temperature to 14.8 g (0.15 mol) of R-(−)-2-amino-1-butanol in 200 ml of anhydrous dioxane and the mixture is heated at 80° C. for 1 h, then at reflux for 1 h. After concentrating in vacuo, crystallized imidazole is filtered off with suction, 100 ml of 1N HCl are added to the filtrate, which is extracted with dichloromethane three times, and the organic phase is dried over MgSO₄. After removing the solvents by distillation, an oily product is obtained.

¹H-NMR (CDCl₃, 60 MHz):

$\delta$ = 6.70 (s (br) NH), 4.23 (t, 1H), 3.80 (m, 2H) 1.55 (m, CH₂), 0.93 (t, CH₃).

b) 2,2-dimethyl-4-(4,R-ethyl-3-oxazolidinyl-2-one)-6-phenylsulfonyl-2H-benzo[b]pyran

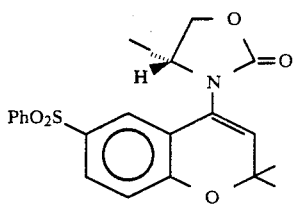

4.5 g (40 mmol) of potassium tert.butylate are added in portions with stirring under a nitrogen atmosphere to 4.6 g (40 mmol) of 4R-ethyl-oxazolidin-2-one in 70 ml of N,N-dimethylacetamide. After 30 minutes, 11.0 g (33 mmol) of 2,2-dimethyl-3,4-dihydro-3,4-epoxy-6-phenylsulfonyl-2H-benzo[b]pyran, dissolved in 25 ml of N,N-dimethylacetamide, are added dropwise at room temperature. The mixture is then heated to 65° C. for 1.5 hours, allowed to cool and poured into 2 l of ice-water. The crystallized crude product is filtered off with suction, taken up in dichloromethane, dried and chromatographed on silica gel using cyclohexane/ethyl acetate (1:1). Appropriate fractions are concentrated and the product is made to crystallize using diethyl ether.

M.p. 149°–151° C.

EXAMPLE 3

2,2-dimethyl-3,4-dihydro-trans[3-hydroxy-4-(4,R-ethyl-3-oxazolidinyl-2-one]-6-phenylsulfonyl-2H-benzo[b]pyran, isomer A 2,2-dimethyl-3,4-dihydro-trans[3-hydroxy-4-(4′R-ethyl-3-oxazolidinyl-2-one,]-6-phenylsulfonyl-2H-[b]pyran, isomer B

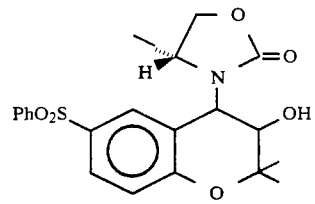

6.3 g (20 mmol) of 2,2,-dimethyl-3,4-dihydro-3,4-epoxy-6-phenylsulfonyl-2H-benzo[b]pyran, 4.1 g (22 mmol) of N-trimethylsilyl-4R-ethyl-oxazolidinyl-2-one (prepared analogously to Example 1a), and 6.9 g (22 mmol) of tetran-butylammonium fluoride trihydrate are reacted analogously to Example 1b), the reaction mixture being stirred at 90° C. for 3 h. After chromatographic separation of the crude product on silica gel (30–70 μm) using cyclohexane/ethyl acetate (2:1), isomer A is obtained from appropriate fractions and made to crystallize using diethyl ether, m.p. 175°–177° C.

¹H-NMR (CDCl₃, 270 MHz): $\delta$ = 6.88 (d, J=9Hz, 1H), 1.55 (s, C—CH₃), 1.23 (s, C—CH₃), 0.67 (t, —CH₂CH₃)

Isomer B is made to crystallize from appropriate fractions.

M.p. 153°–155° C. (diethyl ether)

¹H-NMR (CDCl₃, 270 MHz): $\delta$ = 6.93 (d, J=9Hz, 1H), 1.48 (s, C—CH₃), 1.23 (s, C—CH₃), 0.84 (t, —CH₂CH₃)

EXAMPLE 4

2,2-dimethyl-3,4-dihydro-trans[3-hydroxy-4-(4′R-ethyl-3-oxazolidinyl-2-one]-6-cyano-2H-benzo[b]pyran, isomer A 2,2-dimethyl-3,4-dihydro-trans[3-hydroxy-4-(4′R-ethyl-3-oxazolidinyl-2-one)]-6-cyano-2H-benzo[b]pyran, isomer B

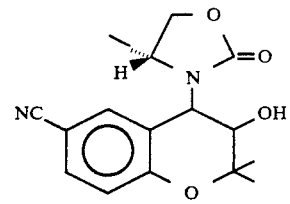

5.0 g (25 mmol) of 2,2-dimethyl-3,4-dihydro-3,4-epoxy-6-cyano-2H-benzo[b]pyran, 4.8 g (25 mmol) of N-trimethylsilyl-4R-ethyl-oxazolidinyl-2-one and 8 g (25 mmol) of tetra-n-butylammonium fluoride trihydrate are reacted analogously to Example 1b), the reaction mixture being stirred at 60° C. for 1.5 hours and at 90° C. for 2 h, N,N-dimethylacetamide is largely removed by distillation in vacuo, saturated aqueous NH₄Cl solution is added to the residue and the mixture is extracted using ethyl acetate. After chromatographic separation of the crude product on silica gel (30–70 μm) using toluene/ethyl acetate, isomer A and isomer B are obtained from appropriate fractions and made to crystallize using diethyl ether.

Isomer A:

M.p. 208°–210° C.

¹H-NMR (CDCl₃, 270 Hz):

δ=7.53 (s, 1H), 7.44 (m, 1H), 6.87 (d, J=9Hz, 1H), 1.58 (s, CH₃), 1.27 (s, CH₃), 0.77 (t, CH₂C$\underline{H}$₃)

Isomer B:

M.p. 166°–168° C. (diethyl ether)

¹H-NMR (CDCl₃, 270 Hz): δ=7.46 (m, 1H), 7.40 (s, 1H), 6.90 (d, J=9Hz, 1H), 1.58 (s, CCH₃), 1.27 (s, C—CH₃), 0.94 (t, CH₂C$\underline{H}$₃)

EXAMPLE 5

2,2-dimethyl-4-(4′R-ethyl-3-oxazolidinyl-2-one)-6-cyano-2H-benzo[b]pyran

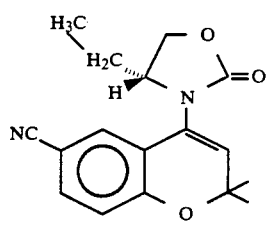

The title compound is obtained from 2,2-dimethyl-3,4-dihydro-3,4-epoxy-6-cyano-2H-benzo[b]pyran and 4R-ethyloxazolidin-2-one as under 2b); colorless crystals M.p. 188°–189° C. (from diethyl ether)

EXAMPLE 6 a) 4R-methyloxazolidin-2-one

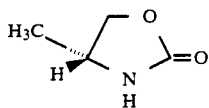

15 g (0.2 mol) of D-alaninol are made to react with 32.5 g (0.2 mol) of N,N-carbonyldiimidazole analogously to Example 2a), m.p. 51°–53° C.

b) 2,2-dimethyl-4-(4′R-methyl-3-oxazolidinyl-2-one)-6-cyano-2H-benzo[b]pyran

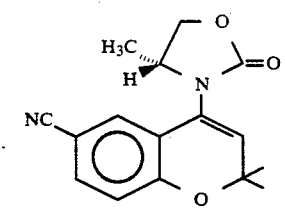

The title compound is obtained from 2,2-dimethyl-3,4-dihydro-3,4-epoxy-6-cyano-2H-benzo[b]pyran and 4R-methyl-oxazolidin-2-one as in 2b); colorless crystals M.p. 195°–197° C. (from diethylether)

EXAMPLE 7 a) N-trimethylsilyl-4R-methyloxazolidin-2-one

The title compound is obtained from 4R-methyloxazolidin-2-one and hexamethyldisilazane analogously to Example 1a),

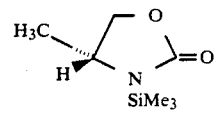

b.p.₂=85° C.
m.p.=46°–48° C.

b) 2,2-dimethyl-3,4-dihydro-6-cyano-trans[3-hydroxy-4-(4′R-methyl-3-oxazolidinyl-2-one)]-2H-benzo[b]pyran, isomer A 2,2-dimethyl-3,4-dihydro-6-cyano-trans[3-hydroxy-4-(4′R-methyl-3-oxazolidinyl-2-one)]-2H-benzo[b]pyran, isomer B

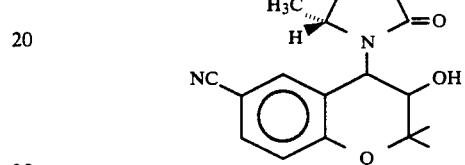

5 g (25 mmol) of 2,2-dimethyl-3,5-dihydro-3,4-epoxy-6-cyano-2H-benzo[b]pyran and 5.2 g (30 mmol) of N-trimethylsilyl-4R-methyloxazolidin-2-one are reacted analogously to Examples 1 and 4 and the crude product is purified by chromatography on silica gel using toluene/ethyl acetate (1:1).

The relatively slow-running isomer A is obtained from appropriate fractions, m.p. 242°–243° C. (ethyl acetate)

¹H-NMR (CDCl₃, 270 MHz): CH₃ signals: δ=1.58 (s), 1.27 (s), 0.96 (d).

A mixed fraction of isomer A: isomer B (about 1:2) obtained by chromatography is made to dissolve in ethanol and then an equivalent amount of water is added. A mixture in which the proportion of A predominates crystallizes from this solution. Isomer B is obtained from the mother liquor in the form of colorless crystals, m.p. 203°–204° C.

¹H-NMR (CDCl₃, 270 MHz): CH₃ signals: δ=1.50 (s), 1.35 (d), 1.25 (s).

EXAMPLE 8 a) N-Trimethylsilyl-4S-methyl-oxazolidin-2-one

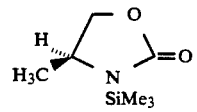

The title compound is obtained from 4S-methyloxazolidin-2-one analogously to Example 1a)

Bp₂=84°–86° C.
M.p.=46°–48° C.

b) 2,2-dimethyl-3,4-dihydro-6-cyano-trans[3-hydroxy-4-(4′S-methyl-3-oxazolidinyl-2-one)]-2H-benzo[b]pyran, isomer A 2,2-dimethyl-3,4-dihydro-6-cyano-trans[3-hydroxy-4-(4′S-methyl-3-oxazolidinyl-2-one)]-2H-benzo[b]pyran, isomer B

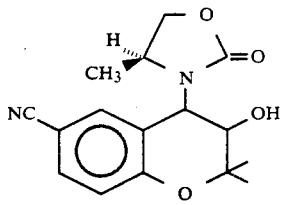

Preparation is carried out analogously to Examples 1, 4 and 7.

Isolation is carried out as described in Example 7b) by column chromatography and crystallization:

Isomer A:
M.p. 241°–243° C.
$^1$-NMR (CDCl$_3$, 270 MHz): CH$_3$ signals: δ=1.58 (s), 1.27 (s), 0.96 (d).

Isomer B:
M.p. 202°–204° C.
$^1$H-NMR (CDCl$_3$, 270 MHz): CH$_3$ signals: δ=1.50 (s), 1.35 (d), 1.25 (s).

EXAMPLE 9

2,2-dimethyl-3,4-dihydro-6-cyano-trans[3-hydroxy-4-(4'R-isopropyl-3-oxazolidinyl-2-one)]-2H-benzo[b]pyran, isomer A
M.p. 226°–228° C. (from ethyl acetate)

2,2-dimethyl-3,4-dihydro-6-cyano-trans[3-hydroxy-4'R-isopropyl-3-oxazolidinyl-2-one)]-2H-benzo[b]pyran, isomer B
M.P. 173°–175° C. (from diethylether)

EXAMPLE 10

2,2-dimethyl-3,4-dihydro-6-cyano-trans[3-hydroxy-4-(4'S-isopropyl-3-oxazolidinyl-2-one)]-2H-benzo[b]pyran, isomer A
M.p. 227°–228° C. (from diethylether)

2,2-dimethyl-3,4-dihydro-6-cyano-trans[3-hydroxy-4-(4'S-isopropyl-3-oxazolidinyl-2-one)]-2H-benzo[b]pyran, isomer B
M.p. 174°–175° C. (from diethylether)

The following compounds of the formula I

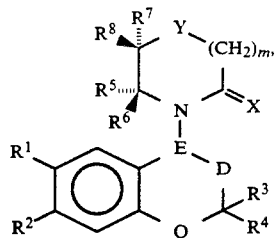

in which E—D stands for CH—CH(OH) as defined under a), m is zero, R$^2$, R$^7$ and R$^8$ are hydrogen, X is oxygen and R$^3$ and R$^4$ are methyl, can be prepared in an analogous manner.

| R$^1$ | R$^5$ | R$^6$ | Y | Isomer |
|---|---|---|---|---|
| CN | i Prop. | H | NMe | A |
| CN | i Prop. | H | NMe | B |
| SO$_2$Me | i Prop. | H | O | A |
| SO$_2$Me | i Prop. | H | O | B |
| SO$_2$Ph | i Prop. | H | O | A |
| SO$_2$Ph | i Prop. | H | O | B |
| CN | H | i Prop. | NMe | A |
| CN | H | i Prop. | NMe | B |
| SO$_2$Me | H | i Prop. | O | A |
| SO$_2$Me | H | i Prop. | O | B |
| SO$_2$Ph | H | i Prop. | O | A |
| SO$_2$Ph | H | i Prop. | O | B |
| CN | CH$_2$CH(CH$_3$)$_2$ | H | O | A |
| CN | CH$_2$CH(CH$_3$)$_2$ | H | O | B |
| SO$_2$Ph | CH$_2$CH(CH$_3$)$_2$ | H | O | A |
| SO$_2$Ph | CH$_2$CH(CH$_3$)$_2$ | H | O | B |
| CN | H | CH$_2$CH(CH$_3$)$_2$ | O | A |
| CN | H | CH$_2$CH(CH$_3$)$_2$ | O | B |
| SO$_2$Me | H | CH$_2$CH(CH$_3$)$_2$ | O | A |
| SO$_2$Me | H | CH$_2$CH(CH$_3$)$_2$ | O | B |
| CN | H | Et | O | A |
| CN | H | Et | O | B |
| SO$_2$Ph | H | Et | O | A |
| SO$_2$Ph | H | Et | O | B |
| SO$_2$Me | Et | H | O | A |
| SO$_2$Me | Et | H | O | B |
| CN | Ph | H | O | A |
| CN | Ph | H | O | B |
| SO$_2$Me | Ph | H | O | A |
| SO$_2$Me | Ph | H | O | B |
| SO$_2$Ph | Ph | H | O | A |
| SO$_2$Ph | Ph | H | O | B |
| CN | H | Ph | O | A |
| CN | H | Ph | O | B |
| SO$_2$Me | H | Ph | O | A |
| SO$_2$Me | H | Ph | O | B |
| SO$_2$Ph | H | Ph | O | A |
| SO$_2$Ph | H | Ph | O | B |
| CN | Bz | H | O | A |
| CN | Bz | H | O | B |
| SO$_2$Me | Bz | H | O | A |
| SO$_2$Me | Bz | H | O | B |
| SO$_2$Ph | Bz | H | O | A |
| SO$_2$Ph | Bz | H | O | B |
| SO$_2$Ph | H | Bz | O | A |
| SO$_2$Ph | H | Bz | O | B |
| CN | Me | H | NBz | A |
| CN | Me | H | NBz | B |
| SO$_2$Me | Me | H | O | A |
| SO$_2$Me | Me | H | O | B |
| SO$_2$Ph | Me | H | O | A |
| SO$_2$Ph | Me | H | O | B |
| CN | H | Me | NBz | A |
| CN | H | Me | NBz | B |
| SO$_2$Ph | H | Me | O | A |
| SO$_2$Ph | H | Me | O | B |
| SO$_2$Me | H | Me | O | A |
| SO$_2$Me | H | Me | O | B |
| CN | Me | H | NMe | A |
| CN | Me | H | NMe | B |
| CN | H | Me | NMe | A |
| CN | H | Me | NMe | B |
| SO$_2$Ph | Me | H | N-nBu | A |
| SO$_2$Ph | Me | H | N-nBu | B |
| CN | Me | H | N-nBu | A |
| CN | Me | H | N-nBu | B |
| CN | i Prop. | H | N-nBu | A |
| CN | i Prop. | H | N-nBu | B |
| CN | Ph | H | NMe | A |
| CN | Ph | H | NMe | B |

We claim:
1. A benzo[b]pyran derivative of the formula I

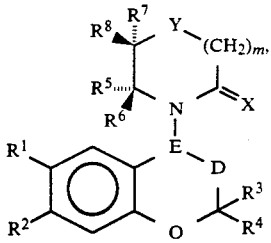

in which
E—D stands for
  a) CH—CH(OH) or
  b) C=CH,
X stands for O or S,
Y stands for O,
$R^1$ stands for CN, $NO_2$, F, Cl, Br, $CF_3$, $(C_1-C_6)$-alkoxy, carbonyl, $SO_n$—$(C_1-C_6)$-alkyl or $SO_n$—Ar; where n=1 or 2, Ar stands for phenyl which is unsubstituted or substituted by to 3 identical or different radicals $(C_1-C_2)$-alkyl, $(C_1-C_2)$-alkoxy, F, Cl, Br, trifluoromethyl, CN, $NO_2$, CO—$(C_1-C_2)$-alkyl or $SO_p$—$(C_1-C_2)$-alkyl, and p stands for 1 or 2,
$R^2$ stands for H,
$R^3$ and $R^4$ are identical or different and stand for alkyl
$R^5$ and $R^6$ are identical or different and stand for hydrogen, or $(C_1-C_4)$-alkyl, p stands for 1 or 2, and f is zero, 1, 2 and 3, where, however, compounds are excluded in which $R^5$ and $R^6$ simultaneously are hydrogen,
$R^7$ and $R^8$ stand for hydrogen,
m is zero, 1 or 2; compounds being excluded, in which simultaneously
  1. m=1
  2. one of the two substituents $R^5$ or $R^6$ is equal to methyl and the other to hydrogen, and
  3. Y is oxygen.

2. A compound I as claimed in claim 1, wherein the following substituents and indices have the following meanings:
  $R^1$, $R^2$, $R^3$ and $R^4$ are as defined in claim 1, and one of the two substituents $R^5$ or $R^6$ is hydrogen or methyl and the other is as defined in claim 1, and
  $R^7$, $R^8$, $R^9$, $R^{10}$, $R^{11}$, m, f, X and Y are as defined in claim 1.

3. A compound I as claimed in claim 1, in which $R^1$ stands for CN, $NO_2$, $SO_2$—$(C_1-C_4)$-alkyl, $(C_1-C_4)$-alkoxycarbonyl, fluorine, chlorine or $CF_3$,
  $R^2$ stands for H
  $R^3$ and $R^4$ stand for methyl and ethyl,
  one of the two substituents $R^5$ and $R^6$ stands for hydrogen or methyl and the other stands for $(C_1-C_4)$-alkyl, or
  p stands for 1 or 2, and
  f is zero, 1, 2 and 3,
  $R^7$ and $R^8$ stand for hydrogen,
  $R^9$ stands for H, $(C_1-C_4)$-alkyl, phenyl or benzyl, where the phenyl ring is unsubstituted or substituted by one or two identical or different radicals from the series $(C_1-C_2)$-alkyl, $(C_1-C_2)$-alkoxy, F, Cl, trifluoromethyl, CN, $NO_2$ and CO—$(C_1-C_2)$-alkyl,
  m=zero or 1,
  X stands for O or S and
  Y stands for O.

4. A compound I as claimed in claim 1, wherein $R^1$ stands for $SO_2$phenyl, where phenyl is unsubstituted or substituted by 1 to 3 substituents from the series consisting of $(C_1-C_2)$-alkyl, $(C_1-C_2)$-alkoxy, F, Cl, Br, trifluoromethyl, CN, $NO_2$, CO—$(C_1-C_2)$-alkyl and $SO_p$—$(C_1-C_2)$-alkyl, and p stands for 1 or 2,
  $R^2$ stands for H
  $R^3$ and $R^4$ stand for methyl and ethyl,
  one of the two substituents $R^5$ and $R^6$ stands for hydrogen or methyl and the other stands for $(C_1-C_4)$-alkyl,
  p stands for 1 or 2, and
  f is zero, 1, 2 and 3,
  $R^7$ and $R^8$ stand for hydrogen,
  $R^9$ stands for H, $(C_1-C_4)$-alkyl, phenyl or benzyl, where the phenyl ring is unsubstituted or substituted by one or two identical or different radicals from the series consisting of $(C_1-C_2)$-alkyl, $(C_1-C_2)$-alkoxy, F, Cl, trifluoromethyl, CN, $NO_2$ and CO—$(C_1-C_2)$-alkyl,
  m is zero or 1,
  X stands for O or S and
  Y stands for O.

5. A compound as claimed in claim 1, wherein E—D is as defined under a) and
  $R^1$ stands for CN or $SO_2CH_3$,
  $R^2$ stands for H,
  $R^3$ and $R^4$ stand for methyl,
  one of the substituents $R^5$ and $R^6$ is hydrogen and the other stands for $(C_1-C_4)$-alkyl, $R^7$ and $R^8$ stand for hydrogen,
  m is zero,
  X stands for O and
  Y stands for O.

6. A compound I as claimed in claim 1, wherein E—D is as defined under a) and
  $R^1$ stands for $SO_2$-phenyl,
  $R^2$ stands for hydrogen,
  $R^3$ and $R^4$ stand for methyl,
  one of the substituents $R^5$ and $R^6$ is hydrogen and the other stands for $(C_1-C_4)$-alkyl, $R^7$ and $R^8$ stand for hydrogen,
  m is zero,
  X stands for O or
  Y stands for O.

7. A method for the treatment of a mammal in need of antihypertensive action which comprises administering to said mammal a pharmaceutically effective amount of a compound I as claimed in claim 1 as an antihypertensive.

8. A pharmaceutical composition having an antihypertensive action which contains a pharmaceutically effective amount of a compound I as claimed in claim 1 together with a pharmaceutically suitable carrier.

9. A method for the treatment of a mammal in need of spasmolytic action which comprises administering to said mammal a pharmaceutically effective amount of a compound I as claimed in claim 1 as a spasmolytic.

10. A pharmaceutical composition having a spasmolytic action, which contains an effective amount of a compound I as claimed in claim 1 together with a pharmaceutically suitable carrier.

11. A method for producing an antihypertensive effect or a spasmolytic effect, which comprises providing an effective amount of a compound I as claimed in claim 1 with the pharmaceutically customary additives.

* * * * *

UNITED STATES PATENT AND TRADEMARK OFFICE
CERTIFICATE OF CORRECTION

PATENT NO. : 5,130,310

DATED : July 14, 1992

INVENTOR(S) : Klaus WEIDMANN et al.

It is certified that error appears in the above-indentified patent and that said Letters Patent is hereby corrected as shown below:

On the Title Page:

Second line, "Weidman et al." should read --Weidmann et al.--;

Item [75] Inventors, "Klaus Weidman" should read --Klaus Weidmann--.

Item [57] ABSTRACT
   line 13, alkylsulfi(i)(o)nyl" should read --alkylsulf(i)(o)nyl--.

Claim 1; col. 17, line 20, "alkoxy, carbonyl" should read --alkoxycarbonyl--;

line 22, "by to 3" should read --by 1 to 3--; and line 28, "stand for alkyl" should read --stand for alkyl having 1-4 C atoms--.

UNITED STATES PATENT AND TRADEMARK OFFICE
CERTIFICATE OF CORRECTION

PATENT NO. : 5,130,310

DATED : July 14, 1992

INVENTOR(S) : Klaus WEIDMANN et al.

It is certified that error appears in the above-indentified patent and that said Letters Patent is hereby corrected as shown below:

Claim 2; col. 17, line 48 should read --$R^7$, $R^8$, m, f, X and Y are as defined in--.

Claim 3, col. 17, line 57 should read --alkyl,--; and line 64 "from the series" should read --from the series consisting of--.

Claim 5, col. 18, line 25, "compound" should read --compound I--.

Claim 6, col. 18, line 45 should read --X stands for O and--.

Signed and Sealed this

Eighth Day of July, 1997

Attest:

BRUCE LEHMAN

Attesting Officer

Commissioner of Patents and Trademarks